US006376440B1

(12) United States Patent
Hennen et al.

(10) Patent No.: US 6,376,440 B1
(45) Date of Patent: Apr. 23, 2002

(54) MOLDED SYNTHETIC COMPOSITIONS

(75) Inventors: Udo Hennen; Evelyn Roseneck; Wolfhard Scholz, all of Krefeld; Werner Schneider, Düsseldorf, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/380,697

(22) PCT Filed: Feb. 21, 1998

(86) PCT No.: PCT/EP98/01011

§ 371 Date: Nov. 29, 1999

§ 102(e) Date: Nov. 29, 1999

(87) PCT Pub. No.: WO98/39408

PCT Pub. Date: Sep. 11, 1998

(30) Foreign Application Priority Data

Mar. 3, 1997 (DE) ........................................ 197 08 605

(51) Int. Cl.[7] ........................................ A61K 7/50
(52) U.S. Cl. ........................ 510/141; 510/155; 510/156
(58) Field of Search ................................ 510/139, 155, 510/156, 151, 153, 152, 141

(56) References Cited

U.S. PATENT DOCUMENTS

| | | | | |
|---|---|---|---|---|
| 4,150,001 | A | 4/1979 | Sen | 252/539 |
| 4,557,853 | A | 12/1985 | Collins | 252/128 |
| 5,496,493 | A | 3/1996 | Cox et al. | 252/174 |

FOREIGN PATENT DOCUMENTS

| | | |
|---|---|---|
| DE | 39 39 579 | 6/1991 |
| DE | 19544453 | 6/1997 |
| EP | 0 266 200 | 5/1988 |
| GB | 689 569 | 4/1953 |
| GB | 731 371 | 6/1955 |
| GB | 1 333 042 | 10/1973 |
| WO | WO95/13357 | 5/1995 |

OTHER PUBLICATIONS

JAOCS, vol. 59, No. 10 (1982) pp. 442–448.
Derwent Patent Abstract (WPAT) No. 91–172154/24. NMA.
Derwent Patent Abstract (WPAT) No. 97–299155/28.

*Primary Examiner*—Necholus Ogden
(74) *Attorney, Agent, or Firm*—Wayne C. Jaeschke; Kimberly R. Hild; Glenn E. J. Murphy

(57) ABSTRACT

A molded synthetic composition is presented having at least 25% by weight synthetic surfactants, at least 30% by weight non-surface-active organic plasticizers and fillers, and 5 to 30% by weight of talcum. The composition provides improved moldability and initial foam quality.

11 Claims, No Drawings

MOLDED SYNTHETIC COMPOSITIONS

This application is filed under 35 U.S.C. 371 and based on PCT/EP98/00474, filed Jan. 29, 1998.

BACKGROUND OF THE INVENTION

1. Field of the Invention

This invention relates to a molded composition based on synthetic surfactants, plasticizers and fillers, preferably in bar form, of which the foam quality is improved by an addition of talcum.

2. Discussion of Related Art

It is known that synthetic surfactants, like soaps produced from fatty acid soaps, can be converted by kneading, milling, extrusion, cutting and bar pressing into a form suitable for transportation or for application and that noodles, granules, bars and handy cakes of toilet soap can be produced in this way.

To this end, the known high-foaming anionic surfactants are normally mixed with plasticizers, fillers and extenders which provide for easier molding and which ensure better dimensional stability.

Unfortunately, many of these substances have an adverse effect on the foaming behavior of the synthetic compositions, more especially their initial foaming behavior. The foam volume, foam stability and foam quality of synthetic compositions are often unsatisfactory.

Accordingly, there has been no shortage of attempts to overcome this deficiency by using suitable surfactant mixtures and additives. An overview of the production of synthetic compositions and known additives can be found in JAOCS, Vol. 59, No. 10 (October 1982), pages 442 to 448. In addition, it is known that builder salts, layer silicates (bentonites) and calcium-binding zeolites can be added to detergent bars which are used for washing laundry.

It is known from DE 39 39 579 A1 that an addition of alkali metal aluminium silicates of the zeolite type improves the moldability and foaming behavior of certain synthetic compositions.

U.S. Pat. No. 4,150,001 describes detergent bars for washing laundry which contain up to 60% by weight of builder salts, 1 to 40% by weight of alkaline earth metal phosphates and talcum to reduce the tendency towards shrinkage.

EP 0 266 200 A2 describes a solid detergent bar of nonionic surfactants for prewashing laundry which may also contain clays, talcum and calcites as carrier component.

It has now been found that an addition of talcum can distinctly improve the moldability and the initial foaming behavior, foam volume and fine-bubble character of the foam in the application of synthetic compositions.

DESCRIPTION OF THE INVENTION

Accordingly, the present invention relates to a molded synthetic composition containing at least 25% by weight of synthetic surfactants and at least 30% by weight of non-surface-active organic plasticizers and fillers which contains from 5 to 30% by weight of talcum to improve its foaming properties and its moldability.

The synthetic surfactants present may be ionic and nonionic surfactants, although high-foaming anionic surfactants should be predominantly used, i.e. more than 15% by weight of such surfactants should be used. Ampholytic, zwitterionic and nonionic surfactants may be additionally present in quantities of up to 10% by weight.

Anionic surfactants containing a linear $C_{12-18}$ alkyl or acyl group and a sulfonate or sulfate group in the form of their alkali metal, magnesium, ammonium or alkanolammonium salts are preferably used in a quantity of 25 to 50% by weight as high-foaming synthetic surfactants. Suitable anionic surfactants may be represented, for example, by general formulae I to IV below:

$$R^1—SO_3^{(-)}M^{(+)} \quad (I)$$

$$R^2O—(EO)_x—SO_3^{(-)}M^{(+)} \quad (II)$$

$$R^3CO(A)—CH_2—CH_2SO_3^{(-)}M \quad (III)$$

$$R^4O\ CO(B)—SO_3^{(-)}M^{(+)} \quad (IV)$$

In these formulae, $R^1$, $R^2$ and $R^4$ are linear alkyl or alkenyl groups containing 10 to 18 carbon atoms while $R^3CO$ is a linear acyl group containing 12 to 18 carbon atoms, (EO) is a $(C_2H_4O)$ or $(C_3H_6O)$ group, x is 0 or a number of 1 to 6, (A) is oxygen or a $CH_3N$ group, (B) is a group $(C_nH_{2n})$, where n=1 to 3, or a group $(—CH—CH_2—COO^{(-)}M^{(+)})$ and M is an alkali metal, $Mg^{+2}$, ammonium or alkanolammonium cation.

Suitable surfactants of formula I are alkane sulfonates and olefin sulfonates; suitable surfactants of formula II are alkyl sulfates and alkyl ether sulfates; surfactants of formula III are acyl isethionates and acyl taurides; suitable surfactants of formula IV are sulfocarboxylic acid esters, for example sulfoacetates, sulfopropionates or sulfosuccinates. Preferred anionic surfactants are, above all, acyl isethionates, sulfosuccinates and mixtures thereof.

Besides anionic surfactants, amphoteric or zwitterionic surfactants may be present in the compositions in small quantities of up to 10% by weight. Suitable amphoteric surfactants are, for example, $C_{12-18}$ alkyl aminopropionic acid or $C_{12-18}$ alkyl aminoacetic acid. Suitable zwitterionic surfactants are, for example, $C_{12-18}$ alkyl dimethyl carboxymethyl aceto-betaine and $C_{12-13}$ acyl amidopropyl dimethyl acetobetaine.

Nonionic surfactants may also be present in the synthetic compositions according to the invention in relatively small quantities of 1 to 10% by weight. Suitable nonionic surfactants are products of the addition of ethylene oxide onto $C_{10-22}$ fatty alcohols, onto $C_{10-22}$ fatty acids, onto fatty acid monoglycerides, onto sorbitan fatty acid monoesters, onto fatty acid triglycerides or onto methyl glucoside fatty acid monoesters. Particularly suitable nonionic surfactants are alkyl (oligo)glycosides corresponding to the formula $R^5O(C_6H_{10}O_5)_y—H$, where $R^5$ is an alkyl group containing 8 to 18 carbon atoms, $(C_6H_{10}O)_y$ is a glucoside unit and y is its average degree of oligomerization of 1 to 5. Alkyl (oligo) glycosides such as these are commercially available, for example under the trademark Plantaren® 2000 CSUP or Plantacare® 2000 CSUP.

Talcum is a hydrated magnesium silicate with the theoretical composition $3MgO·4SiO_2·H_2O$ or $Mg_3(Si_4O_{10})·(OH)_2$ which may also contain hydrated magnesium aluminium silicate in a quantity capable of making up an $Al_2O_3$ content of up to 12% by weight.

The particle diameter (equivalent spherical diameter) of the talcum should be in the range from 0.5 to 50 $\mu$m. In general, talcum qualities containing no more than 5% by weight of particles smaller than 1 $\mu$m in size and no more than 5% by weight of particles larger than 50 $\mu$m in size have proved to successful. The percentage content of particles larger than 40 $\mu$m in diameter (sieve residue) is at most 2% by weight; the mean particle diameter is preferably 5 to 15 $\mu$m.

The impurity content should be no more than 1.6% by weight $Fe_2O_3$, 1% by weight CaO and 1% by weight non-combined water (drying loss at 105° C.). The content of hydrated magnesium aluminium silicate may be as high as 60% by weight (expressed as $Al_2O_3$ up to 12% by weight).

The synthetic composition according to the invention is preferably free from fatty acid soaps, although quantities of less than 10% by weight of fatty acids in the form of the soap are tolerable.

Suitable non-surface-active organic plasticizers and refatting agents are, for example,

- free fatty acids containing 16 to 22 carbon atoms,
- fatty alcohols containing 16 to 22 carbon atoms and
- fatty acid esters such as, for example, hydrogenated fats (triglycerides), waxes, glycerol monostearate, glycol distearate,
- paraffins.

Suitable organic fillers are, for example, carbohydrates (starch, dextrins, sugars), sorbitol, mannitol, urea, proteins and protein hydrolyzates and polyethylene glycols (Carbowax®).

The synthetic compositions according to the invention preferably contain 30 to 50% by weight of non-surface-active organic plasticizers and fillers from the group of $C_{12-22}$ fatty alcohols, free $C_{16-22}$ fatty acids, fatty acid esters, paraffins and carbohydrates or mixtures thereof.

In addition, the synthetic compositions according to the invention may contain the following ingredients in small quantities of up to—in all—5% by weight as further auxiliaries:

- complexing agents
- antimicrobial agents, preservatives
- dyes, pigments ($TiO_2$), opacifiers and flatting agents
- perfumes
- salts, for example $Na_2SO_4$, $NaH_2PO_4$, $Na_5P_3O_{10}$
- antioxidants
- dermatological or cosmetic active substances (for example skin moisturizers, such as Na lactate, pyrrolidone carboxylic acid, glycerin).

The synthetic compositions according to the invention may also contain water. However, the water content of the synthetic composition should be below 10% by weight. In a preferred embodiment, the synthetic composition contains about 5 to 10% by weight of water.

In one particularly preferred embodiment, the synthetic compositions according to the invention contain:

- 30 to 40% by weight of anionic surfactants from the group of acyl ise-thionate salts, sulfosuccinic acid monoalkyl ester salts or mixtures thereof,
- 30 to 50% by weight of organic plasticizers and fillers from the group of fatty alcohols, free fatty acids, fatty acid esters, paraffins and starch,
- 10 to 30% by weight of talcum and
- 5 to 10% by weight of water.

The molded synthetic compositions according to the invention may be produced by any of the methods normally used for such products, the combination according to the invention of synthetic surfactants and talcum giving a particularly moldable composition which is plastic when hot and hard after cooling. The molded products have a smooth surface which, even after wetting with water, dries again without becoming soft.

Conventional processes for mixing or homogenizing, kneading and optionally milling, extruding, optionally pelleting, extruding, cutting and bar pressing, which are described for example in JAOCS, Vol. 59, No. 10 (October 1982), 442–448, may also be used for the production of the synthetic soap compositions according to the invention.

The following procedure has proved successful for the production of synthetic toilet soaps based on the synthetic composition according to the invention:

The meltable components, for example the fatty acid, the fatty alcohol, the alkyl (oligo)glucoside and the meltable or liquid plasticizers, are melted and heated at a temperature of 60 to 90° C. in a heatable kneader or mixer. The anionic surfactant, for example the $C_{12-18}$ acyl isethionate salt, optionally the sulfosuccinate and the starch and other components which do not melt at 60 to 90° C. and optionally the water are then added and the whole is mixed or kneaded at a temperature of around 70° C.

Further homogenization can be achieved by pressing the composition repeatedly through sieves and finally extruding it at a head temperature of 40 to 70° C. to form a strand which is cut into uniform pieces. Finally, the pieces may be converted into the final shape in a molding press.

Instead of being extruded into a strand, the composition may also be extruded through a multiple-bore die which results in the formation of noodles or needles or, where the die is followed by a blade, granules.

The following Examples are intended to illustrate the invention without limiting it in any way.

EXAMPLES

Synthetic compositions according to the invention
1.1 The following raw materials were used

| | |
|---|---|
| Isethionate: | sodium-$C_{12-18}$-acyl isethionate (Sodium Cocoyl Isethionate) |
| Sulfosuccinate: | sulfosuccinic acid mono-$C_{12-18}$-alkyl ester disodium salt |
| Texapon ® K12: | Na lauryl-($C_{12-18}$)-sulfate |
| Plantacare ® 2000 UP: | $C_{8-16}$ alkyl (oligo)glucoside, DP degree x = 1.4 (50% in $H_2O$) |
| Steasilk ® 5 AE: | talcum (hydrous magnesium silicate)<br>$SiO_2$: 63%, MgO: 31.4%, $Al_2O_3$: 0.1%, $Fe_2O_3$: 0.2%, CaO: 0.4%<br>Particie size distribution:<br>5% by weight smaller than 0.9 μm<br>5% larger than 10 μm<br>sieve residue 45 μm: max. 0.1% |
| Vitamin F (water-soluble): | linolenic acid with Polysorbate 20 |

1.2 Production Process

The synthetic soaps were produced in a heatable kneader. The components were heated to 90° C. and intensively mixed. After cooling to 40° C., the perfumes were added. After brief mixing, the composition was transferred to an extruder.

1.3 Formulations

The synthetic compositions produced according to the formulations in the following Table showed very rapid initial foaming and formed a rich and consistent foam of fine bubbles.

TABLE

| Formulations | 1 | 2 | 3 |
|---|---|---|---|
| Isethionate | 17 | 14 | 20 |
| Sulfosuccinate | 17 | 14 | — |
| Texapon ® K12 | 2 | 1.5 | 20 |
| Plantacare ® 2000 UP | 5 | 4 | — |
| Stearic acid | 5 | 4 | — |
| Cetyl/stearyl alcohol (1:1) | 12 | 10 | 11 |
| Hydrogenated castor oil | 5 | 4 | — |
| Glycerin | 6 | 5 | 5 |
| Wheat starch meal | 10 | 8 | 15 |
| Steasilk ® 5 AE | 10 | 25 | 15 |

TABLE-continued

| Formulations | 1 | 2 | 3 |
|---|---|---|---|
| Paraffin wax | — | — | 7 |
| Paraffin oil | 2 | 1.5 | — |
| Squalane | 0.1 | 0.1 | 0.1 |
| Vitamin F water-soluble | — | — | 0.1 |
| Panthenol | 0.1 | 0.1 | 0.1 |
| Citric acid | — | — | 1.0 |
| Lactic acid (80% in $H_2O$) | — | — | 0.5 |
| Na lactate (50% in $H_2O$) | 0.2 | 0.2 | 0.2 |
| Titanium dioxide | 1.2 | 1.2 | 1 |
| Water | 6.2 | 6.2 | 3 |
| Perfume oil | 1.2 | 1.2 | 1 |

The following raw materials or commercial products were used:

| | |
|---|---|
| Texapon ® K12: | cocofatty alcohol ($C_{12-18}$) sulfate, Na salt |
| Plantacare ® 2000 UP: | alkyl ($C_{8-16}$) oligo(1,4)glucoside |
| Steasil ® 5 AE: | talcum powder |
| Vitamin F (water-soluble): | linolenic acid with POE 20 sorbitan monolaurate |

What is claimed is:

1. A molded synthetic composition in bar form comprising:

(a) at least 25 percent by weight of a synthetic surfactant, wherein the synthetic surfactant comprises at least one anionic surfactant having a formula III, IV or combinations thereof $$R^3CO(A)—CH_2—CH_2SO_3^{(-)}M \quad (III)$$

$$R^4O\ CO(B)—SO_3^{(-)}M^{(+)} \quad (IV)$$

wherein $R^3CO$ is a linear acyl group containing 12 to 18 carbon atoms, $R^4$ is a linear alkyl or alkenyl group containing 10 to 18 carbon atoms, (A) is oxygen or a $CH_3N$ group, (B) is a $(C_nH_{2n})$ group, where n is 1 to 3, or a (—CH—$CH_2$—$COO^{(-)}M^{(+)}$) group and M is an alkali metal, $Mg^{+2}$, ammonium or alkanolammonium cation;

(b) at least 30 percent by weight of a non-surface-active organic plasticizer or filler; and (c) 5 to 30 percent by weight of talcum.

2. The molded synthetic composition of claim 1 comprising 30 to 50 percent by weight of the non-surface-active organic plasticizer or filler selected from the group consisting of $C_{12-22}$ fatty alcohols, free $C_{16-22}$ fatty acids, fatty acid esters, paraffins, and carbohydrates.

3. The molded synthetic composition of claim 1, wherein the talcum comprises particles having a particle diameter of from 0.5 to 50 micrometers.

4. The molded synthetic composition of claim 1 further comprising water in an amount of up to 10 percent by weight.

5. A molded synthetic composition in bar form comprising:

(a) 30 to 40 percent by weight of an anionic surfactant comprising one or more acyl isethionate salts, sulfosuccinic acid monoalkyl ester salts or mixtures thereof;

(b) 30 to 50 percent by weight of organic plasticizers and fillers selected from the group consisting of fatty alcohols, free fatty acids, fatty acid esters, paraffins and starch;

(c) 10 to 30 percent by weight of talcum; and (d) 5 to 10 percent by weight of water.

6. The molded synthetic composition of claim 1 wherein the synthetic surfactant comprises 1 weight percent to 10 weight percent of a nonionic surfactant, based on the total weight of the composition.

7. The molded synthetic composition of claim 1, wherein the synthetic surfactant comprises an amphoteric or a zwitterionic surfactant in an amount up to 10 weight percent, based on the total weight of the composition.

8. The molded synthetic composition of claim 1 wherein the non-surface-active organic plasticizer or filler is present in an amount from 30 weight percent to 50 weight percent, based on the total weight of the composition.

9. The molded synthetic composition of claim 8 wherein the anionic surfactant comprises one or more acyl isethionates, acyl taurides or sulfocarboxylic acid esters, or combinations thereof.

10. The molded synthetic composition of claim 9 wherein the anionic surfactant comprises one or more acyl isethionates or sulfosuccinates, or combinations thereof.

11. The molded synthetic composition of claim 1 wherein the molded composition is a toiletry soap.

* * * * *